United States Patent [19]
Kunkel et al.

[11] Patent Number: 5,413,778
[45] Date of Patent: May 9, 1995

[54] LABELLED MONOCYTE CHEMOATTRACTANT PROTEIN MATERIAL AND MEDICAL USES THEREOF

[75] Inventors: Steven L. Kunkel, Ann Arbor, Mich.; Leon R. Lyle, Webster Groves, Mo.; Robert M. Strieter, Ann Arbor, Mich.

[73] Assignees: The Regents of the University of Michigan, Ann Arbor, Mich.; Mallinckrodt Medical, Inc., St. Louis, Mo.

[21] Appl. No.: 956,862

[22] Filed: Oct. 5, 1992

[51] Int. Cl.$^6$ .............................. A61K 49/02
[52] U.S. Cl. .................. 424/1.41; 530/402; 530/408; 530/409
[58] Field of Search .................. 424/1.1, 9, 1.41; 930/141, 280, 22; 530/300, 324, 351, 402, 408, 409

[56] References Cited

U.S. PATENT DOCUMENTS

| | | | |
|---|---|---|---|
| 4,276,280 | 6/1981 | Akerkar et al. | 424/1.1 |
| 4,520,112 | 5/1985 | Snyder et al. | 436/504 |
| 4,656,280 | 4/1987 | Garlick | 424/1.1 X |
| 4,659,839 | 4/1987 | Nicolotti et al. | 424/1.1 X |
| 4,732,974 | 3/1988 | Nicolotti et al. | 424/1.1 X |
| 4,837,003 | 6/1989 | Nicolotti | 424/1.1 |
| 4,926,869 | 5/1990 | Rubin et al. | 424/1.1 X |
| 4,965,392 | 10/1990 | Fritzberg et al. | 424/1.1 X |
| 4,986,979 | 1/1991 | Morgan, Jr. et al. | 424/1.1 |
| 5,037,630 | 8/1991 | Fritzberg et al. | 424/1.1 |
| 5,079,228 | 1/1992 | Cohen et al. | 530/324 X |
| 5,179,078 | 1/1993 | Rollins et al. | 530/324 X |
| 5,196,510 | 3/1993 | Rodwell et al. | 424/1.1 X |
| 5,198,424 | 3/1993 | McEver | 530/324 X |
| 5,241,049 | 8/1993 | Goodman et al. | 530/350 |

FOREIGN PATENT DOCUMENTS

| | | | |
|---|---|---|---|
| 0284071 | 9/1988 | European Pat. Off. | A61K 49/02 |
| 9002762 | 3/1990 | WIPO | |
| 9013317 | 11/1990 | WIPO | A61K 49/02 |
| 9116919 | 11/1991 | WIPO | |
| 9204372 | 3/1992 | WIPO | |

OTHER PUBLICATIONS

Chem. Abs. 113(13):113534x (1990) Yoshimura et al., J. Immunol., vol. 145, No. 1 pp. 292–297.
R. Ross, "The Pathogenesis of Atherosclerosis", N. Eng. J. Med. 314, pp. 488–500 (1986).
T. J. Standford, B&BRC, vol. 171, pp. 531–536 (1990).
V. M. Elner, Am J. Pathol, vol. 136, pp. 745–750 (1990).
A. J. Thronton, J. Immunol, vol. 144, pp. 2609–2613 (1990).
A. K. Samanta, J. Exp. Med., vol. 169, pp. 1185–1189 (1989).
C. A. Herbert et al., J. Immunol. vol. 145, pp. 3033–3040 (1990).
P. M. Grob, JBC, vol. 265, pp. 8311–8316 (1990).
J. Besemer, et al., JBC, vol. 264, pp. 17409–17415 (1989).
Robinson, et al., "Complete Amino Acid . . . Immune Reactions", Proc. Natl. Acad. Sci. USA, vol. 86, pp. 1850–1854, Mar. 1989.
Nelken, et al., "Monocyte Chemoattractant . . . Atheromatous Plaques", J. Clin. Invest., vol. 88, pp. 1121–1127, Oct. 1991.
Jiang, et al., "Monocyte Chemoattractant . . . In Human Monocytes", The Journal of Immunology, vol. 148, No. 8, pp. 2423–2428, Apr. 1992.
J. Wang, et al., "Human Recombinant Macrophase Inflammatory Protein-1α and -β and Monocyte Chemotactic and Activating Factor . . . " J. Immunol., vol. 150, No. 7, pp. 3022–3029, (Apr. 1, 1993).
K. Neote, et al., "Identification of a Promiscuous Inflammatory Peptide Receptor . . . ", J. Bio. Chem., vol. 268, No. 17, pp. 12247–12239 (Jun. 15, 1993).

Primary Examiner—Robert L. Stoll
Assistant Examiner—Lara E. Chapman
Attorney, Agent, or Firm—Rothwell, Figg, Ernst & Kurz

[57] ABSTRACT

A method of imaging a target site in an animal's body in which a labelled CC chemokine or Monocyte Attractant Protein (MCP) material is introduced into the animal's body and allowed to accumulate at a target site which includes MCP receptor molecules. The accumulated, labelled MCP material is then detected so as to image the target site of the body.

25 Claims, No Drawings

LABELLED MONOCYTE CHEMOATTRACTANT PROTEIN MATERIAL AND MEDICAL USES THEREOF

BACKGROUND OF THE INVENTION

1. Field of the Invention

The present invention relates to the field of labelled peptides, peptides carrying radioactive agents, and medical uses thereof.

2. Description of the Background Art

Labelled peptides and peptides carrying radioactive agents have various therapeutic and diagnostic medical uses. Peptides carrying radioactive agents are known to be therapeutically useful in the treatment of tumors.

An important diagnostic use of labelled peptides is as imaging agents. For example, U.S. Pat. No. 4,926,869 to Rubin et al. discloses detection of an inflammation site in an individual by administering to the individual a labelled immunoglobulin or fragment thereof. The labelled immunoglobulin accumulates at the site of inflammation, thereby permitting radiographic imaging of the site utilizing known imaging techniques.

Other publications which describe the imaging of sites of infection or inflammation, utilizing labelled peptides and peptides carrying radioactive agents, include International Patent Publication Nos. WO 90/10463 and WO 90/13317.

There remains a need in the art for labelled peptides and peptides carrying radioactive agents which can be utilized for medical purposes.

SUMMARY OF THE INVENTION

In accordance with the present invention, a labelled CC chemokine is utilized to image a target site in an animal's body. The labelled CC chemokine is introduced into the animal's body, and allowed to accumulate at the target site, which has complementary Monocyte Chemoattractant Protein (MCP) receptor molecules. The accumulated, labelled CC chemokine then is detected so as to image the target site.

DETAILED DESCRIPTION OF THE PREFERRED EMBODIMENTS

The present invention utilizes a Monocyte Chemoattractant Protein (MCP) material, such as Monocyte Chemoattractant Protein-1 (MCP-1), a member of the CC family of chemotactic cytokines (or chemokines), an analog, homolog, derivative or fragment thereof, or a peptide having specificity for a receptor of MCP-1 (hereinafter sometimes referred to collectively as CC chemokines, Monocyte Chemoattractant Protein material or MCP material). In addition to MCP-1 other CC chemokines include: $MIP_\alpha$, $MIP_\beta$, RANTES, I-309, MCP-2 (also known as HC14), MCP-3 and at least one other CC chemokine which has not yet been completely characterized.

Labelled MCP material in accordance with the present invention can be utilized to image sites of infection, inflammation, restenosis and atheromatous lesions in the body. Such sites include MCP receptor molecules having areas which are complementary to corresponding MCP material.

Restenosis and the development of atheromatous lesions share the common pathological element of proliferation of vascular smooth muscle. Growth factors which induce this proliferation arise from monocytes which infiltrate the area in response to inflammatory stimuli. MCP-1 is a cytokine which is produced by injured vascular smooth muscle and is a potent stimulator of monocyte chemotaxis with very high specificity for monocytes and macrophage cells, which have complementary MCP receptor molecules.

In preferred embodiments, the MCP material utilized in accordance with the present invention is human MCP-1, or an analog, homolog, fragment or derivative thereof.

Human MCP-1 is about 76 amino acid residues in length with a molecular weight of approximately 12.5 kD. The amino acid sequence of MCP-1 is shown below:

$NH_2$ X P D A I N A P V T C C Y N F T N R K I S V Q R
L A S Y R R I T S S K C P K E A V I F K T I V A K
E I C A D P K Q K W V Q D S M D H L D K Q T Q P
K T COOH, wherein the letters between the $NH_2$ group and the COOH group represent amino acids as follows: A represents Alanine, R represents Arginine, N represents Asparagine, D represents Aspartic acid, C represents Cysteine, Q represents Glutamine, E represents Glutamic acid, G represents Glycine, H represents Histidine, I represents Isoleucine, L represents Leucine, K represents Lysine, F represents Phenylalanine, P represents Proline, S represents Serine, T represents Threonine, W represents Tryptophan, X represents a variable amino acid, Y represents Tyrosine and V represents Valine, or a suitable derivative thereof.

The present invention is further applicable to derivatives of MCP material in which retroinverse or other non-hydrolyzable linkages have been inserted, or D-amino acids substitutions have been made, in order to modify the native sequence.

In preferred embodiments, the MCP material carries a label or radioactive agent such as indium, iodine, technetium, rhenium, gallium, samarium, holmium, yttrium, copper, cobalt and the like. In particularly preferred embodiments, the MCP material carries a radioactive label selected from the group consisting of technetium-99m, indium-111, copper-62, iodine-123, iodine-131, rhenium-168 and rhenium-188.

In another embodiment, the labelling agent is a stable isotope such as carbon-13, so as to permit detection of sites of infection, inflammation, atheromatous lesion or restenosis by magnetic resonance spectroscopy.

The MCP material can employ any suitable means for carrying the label or radioactive agent. Known methods for labelling peptides include the conventional "post-formed chelate approach" and the more recent "pre-formed chelate approach" developed by Fritzburg et al., U.S. Pat. Nos. 4,965,392 and 5,037,630, incorporated herein by reference. In the "pre-formed approach," the chelating agent is complexed with a radionuclide and then conjugated to the peptide. In the "post-formed approach," the chelating agent is first conjugated to the peptide and the resulting conjugate is incubated with radionuclide along with a reducing agent.

Suitable chelating agents for use in the present invention include triamide thiolate ($N_3S$) chelating agents such as represented by formula (I) and (Ia) below, diamide dithiolate ($N_2S_2$) chelating agents such as represented by formula (II) below and diamide diphenolic chelating agents such as represented by formula (III) below:

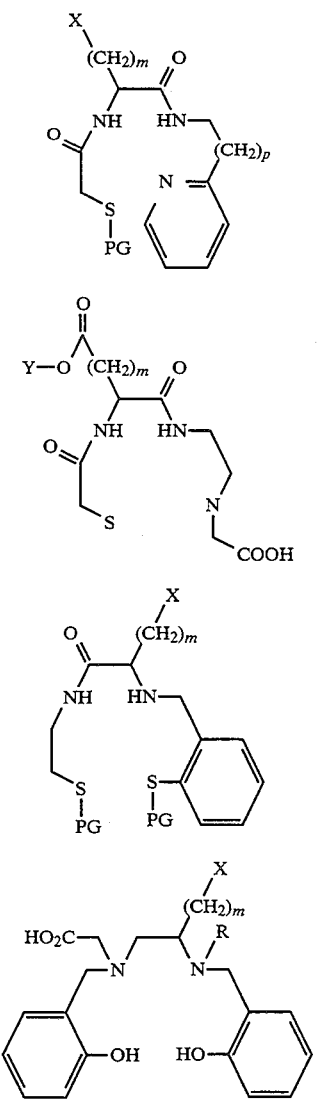

Wherein m in formulas (I), (Ia), (II) and (III) is a whole number of from 1 to about 10 (in formulas (I), (Ia) and (II), m preferably is about 3); P in formula (I) is either 0 or 1; Y of formula (Ia) is o- or p-nitrophenyl, 2-chloro-4-nitrophenyl, cyanomethyl, 2-mercaptopyridyl, hydroxybenztriazole, N-hydroxysuccinimide, trichlorophenyl, tetrafluorophenyl, thiophenyl, tetrafluorothiophenyl, tetrafluorophenyl, thiophenyl, tetrafluorophenyl, o-nitro-p-sulfophenyl or N-hydroxyphthalimide, most preferably tetrafluorophenyl; PG in formulas (I) and (II) is a suitable sulfur protecting group (each of which may be the same or different in formula II) selected from the group consisting of S-acyl groups of from 1 to about 20 carbon atoms such as alkanoyl, benzoyl and substituted benzoyl (wherein alkanoyl is preferred), S-alkyl groups of from 1 to about 20 carbon atoms such as benzyl, t-butyl, trityl, 4-methoxybenzyl and 2,4-dimethoxybenzyl (wherein 2,4-dimethoxybenzyl is preferred), alkoxyalkyl groups of from 1 to about 10 carbon atoms such as methoxymethyl, ethoxyethyl and tetrahydropyranyl (wherein tetrahydropyranyl is preferred), carbamoyl, and alkoxy carbonyl groups of from 1 to about 10 carbon atoms such as t-butoxycarbonyl, methoxycarbonyl and ethoxycarbonyl (wherein t-butoxycarbonyl is preferred); X is a coupling moiety selected from the group consisting of carboxyl, amino, isocyanate, isothiocyanate, imidate, maleimide, chlorocarbonyl, chlorosulfonyl, succinimidyloxycarbonyl, haloacetyl, and N-alkoxycarbamoyl groups of from 1 to about 10 carbon atoms such as N-methyoxycarbamoyl and t-butoxycarbamoyl (wherein in formulas (I) and (II), N-methoxycarbamoyl is preferred); and R of formula (III) is selected from the group consisting of hydrogen and alkyl groups of from 1 to about 10 carbon atoms such as methyl and t-butyl (wherein t-butyl is preferred).

Suitable sulfur-protecting groups, when taken together with the sulfur atom to be protected, include hemithioacetal groups such as ethoxyethyl, tetrahydrofuranyl, methoxymethyl, and tetrahydropyranyl. Other suitable sulfur protecting groups are acyl groups of from 1 to about 20 carbon atoms, preferably alkanoyl or benzoyl. Other possible chelating compounds are described in the European Patent Application assigned publication number 0 284 071 incorporated herein by reference.

Synthesis of a radiolabelled chelating agent, such as a Tc-99m bifunctional chelate, and subsequent conjugation to the MCP material, can be performed as described in European Patent Application publication number 0 284 071 (supra), U.S. Pat. No. 4,965,392 (supra), and related technologies as covered by U.S. Pat. No. 4,837,003, 4,732,974 and 4,659,839, each incorporated herein by reference.

In accordance with one embodiment, the present invention comprises an MCP material conjugated with an unlabelled chelating agent, which later can be chelated with a suitable label or radioactive agent.

MCP material can also be labelled with halogen isotopes such as iodine-123 and iodine-131 using oxidation reactions.

In preferred embodiments utilizing a halogen label, MCP material is labelled with a radioactive halogen such as iodine-123 or iodine-131 utilizing chloramine-T hydrate.

In accordance with the present invention, the MCP material can be utilized to carry a label or radioactive agent to a target site of an animal, such as a human or other mammal.

In particularly preferred embodiments, radiolabelled MCP material is injected into an animal's body and allowed to accumulate at a target site of infection, inflammation, atheromatous lesion or restenosis. As noted above, MCP-1 has a high degree of specificity for monocytes and macrophage cells, and is a potent stimulator of monocyte chemotaxis. Accordingly, radiolabelled MCP-1 is particularly suitable for imaging sites of infection, inflammation, atheromatous lesion or restenosis in the body.

The radiolabelled MCP material is injected into the subject in a pharmaceutically acceptable carrier, such as an aqueous medium.

Pharmaceutically acceptable carriers include those that are suitable for injection or administration such as aqueous buffer solutions, e.g. tris (hydroxymethyl) aminomethane (and its salts), phosphate, citrate, bicarbonate, and the like, sterile water for injection, physiological saline, and balanced ionic solutions containing chloride and/or bicarbonate salts of normal blood plasma cations such as $Ca^{2+}$, $Na^{+}$, $K^{+}$, and $Mg^{2+}$. The carriers may contain a chelating agent, e.g. a small amount of ethylenediaminetetraacidic acid, calcium disodium salt, or other pharmaceutically acceptable chelating agents.

Generally, a diagnostically effective dosage of radiolabelled MCP material will vary depending on considerations such as age, condition, sex, and extent of disease in the subject individual, counter indications, if any, and variables, to be adjusted by the individual physician. For example, dosage can vary from about 0.01 mg/kg to about 2000 mg/kg, and in more preferred embodiments from about 0.1 mg/kg to about 1000 mg/kg.

The radiolabelled MCP material begins to accumulate within approximately 15 minutes after injection into the subject, and in vivo imaging can be performed utilizing conventional imaging equipment for up to 24 hours or more after injection. Known imaging methods include conventional gamma camera techniques, single photon emission computerized tomography (SPECT), and other radionuclide scans.

After accumulating at the target site, the labelled MCP material is gradually cleared from the target site and the animal's system by normal bodily function.

The invention is further illustrated by the following examples, which are not intended to be limiting.

EXAMPLE 1

A solution of MCP material such as MCP-1 (0.01 mmol), in 2 mL of carbonate/bicarbonate buffer at pH 8.5±0.5 is treated with a solution of 0.1 mmol of the ligand of formula I above (wherein m=2, p=1, PG is benzoyl, and X is succinimidyloxycarbonyl) in dimethylformamide (0.5 mL) and the entire mixture is kept at room temperature for 2 hours. The mixture is then diluted with water (2.5 mL) and dialyzed extensively against water or 0.1M ammonium bicarbonate, pH 7.5. After dialysis, the solution is lyophilized to give the desired MCP conjugate.

EXAMPLE 2

A solution of MCP material such as MCP-1 (0.01 mmol), in 2 mL of carbonate/bicarbonate buffer at pH 8.5±0.5 is treated with a solution of 0.1 mmol of the ligand of formula (II) above (wherein m=2, both PG are benzoyl, and X is succinimidyloxycarbonyl) in dimethylformamide (0.5 mL) and the entire mixture is kept at room temperature for 2 hours. The mixture is then diluted with water (2.5 mL) and dialyzed extensively against water or 0.1M ammonium bicarbonate, pH 7.5. After dialysis, the solution is lyophilized to give the desired MCP conjugate.

EXAMPLE 3

A solution of MCP material such as MCP-1 (0.01 mmol) in 2 mL of carbonate/bicarbonate buffer at pH 8.5±0.5 is treated with a solution of 0.1 mmol of the ligand of formula (III) above (wherein m=4, X is succinimidyloxycarbonyl and R is hydrogen) in dimethylformamide (0.5 mL) and the entire mixture is kept at room temperature for 2 hours. The mixture is then diluted with water (2.5 mL) and dialyzed extensively against water or 0.1M ammonium bicarbonate, pH 7.5. After dialysis, the solution is lyophilized to give the desired MCP conjugate.

EXAMPLE 4

To 100 uL of a solution containing 5 mg of sodium gluconate and 0.1 mg of stannous chloride in water, 500 ul of 99m-Tc04 (pertechnetate) is added. After incubation for about 10 minutes at room temperature, a solution of 500 uL of the MCP conjugate (1 mg/mL in 0.1M carbonate/bicarbonate buffer, pH 9.5) of Example 1 or 2 is then added and the entire mixture is incubated at 37° C. for about 1 hour. The desired labelled peptide is separated from unreacted 99mTc-gluconate and other small molecular weight impurities by gel filtration chromatography (Sephadex G-50) using phosphate buffered physiological saline, (hereinafter PBS), 0.15M NaCl, pH 7.4 as eluent.

EXAMPLE 5

A mixture of gentisic acid (25 mg), inositol (10 mg), and the MCP conjugate of Example III (500 uL, 1 mg/mL in water) is treated with In-111 indium chloride in 0.05M HCl. The solution is allowed to incubate at room temperature for about 30 minutes. The desired labelled peptide is separated from unreacted In-111 indium salts and other small molecular weight impurities by gel filtration chromatography (Sephadex G-50) using phosphine buffered physiological saline, (PBS), 0.15M NaCl as eluent.

EXAMPLE 6

Radioiodination of MCP-1, chloramine-T hydrate method.

The following reagents and materials are prepared for radioiodination of MCP-1:
A) Chloramine-T Hydrate (freshly prepared) (FW=227.7) (Store stock desiccated, in vacuo, in dark, ambient temperature)
  1. Weigh out 10.0 mg and dilute with 5.0 ml of 0.05M Phosphate Buffer, pH 6.8.
  2. Take 1.0 ml of dilution and add 9.0 ml 0.05M Phosphate Buffer, pH 6.8 in volumetric flask.
  3. Concentration=0.2 mg/ml; use 45 $\mu$/exp.=39.5 nmoles.
B) 0.05M Sodium Phosphate Buffer, Dibasic, pH 6.8. (FW=268.07) (For Chloramine-T, Metabisulfite, dilution and Reaction).
  1. Weigh out 1.3404 gm and dilute to 80 ml (H$_2$O).
  2. Adjust pH to 6.8, bring to total volume of 100 ml in volumetric flask.
C) 0.25M Sodium Phosphate Buffer, Dibasic, pH 6.8. (FW=268.07) (Reagent for buffering NaI-123 during reaction).
  1. Weigh out 6.7018 gm and dilute to 80 ml (H$_2$O).
  2. Adjust pH to 6.8, bring to total volume of 100 ml in volmeric flask.
D) Sodium Metabisulfite (Freshly Prepared) (FW=190.1).
  1. Weigh out 20.0 mg and dilute with 5.0 ml of 0.05 M Sodium Phosphate Buffer.
  2. Take 1.0 ml of this solution and add 9.0 ml 0.05M Sodium Phosphate Buffer.
  3. Concentration=0.4 mg/ml; use 45 $\mu$l=18.0 $\mu$g/exp.=94.5 nmoles.
E) Phosphate Buffered Saline
  1. Dissolve Sigma (PBS) prepared powder in 1.0 liter of millipore H$_2$O. Sigma cat. #1000-3.
  2. Check pH, should be 7.4.
F) BioRad AG1-X8 Anion Resin 100-200 mesh, Acetate form.
  1. Prepare slurry by suspending 6.4 gms of resin in 10 ml PBS.
G) Potassium Iodide Solution (For testing Chloramine-T solution before use in reaction)

1. Weight out 0.25 gm KI and dilute with 5.0 ml (H₂O).
2. Add several drops of the Chloramine-T solution to the KI solution.
3. A color change from a clear to light yellow solution should be observed, if the Chloramine-T solution is reactive.

H) Microfuge Tubes
1. Sigma siliconized, 1.7 ml, polyproylene, Cat. #T-3406.

I) Sodium Iodine-123
1. Mallinckrodt Medical, Inc.

J) MCP-1 (assuming FW=12,500)
1. Use 10 μg per radioiodination=1.25 nmoles. Pepro Tech Inc.

The following preparations are undertaken prior to running the reaction:

A slurry is prepared of 90% v/v BioRad AG1-X8, 100–200 mesh, acetate form, 24 hours prior to use, with Phosphate Buffered Saline. 2.0 ml of the slurry is poured into a small AG1-X8 column, which then is washed with 10.0 ml Phosphate Buffered Saline. 45.0 μl Chloramine-T (freshly prepared), is pre-drawn into a Hamilton syringe after testing it with 5.0% KI. 45.0 μl Metabisulfite (freshly prepared) is pre-drawn into a Hamilton syringe. 50.0 μl Phosphate Buffered Saline is pre-drawn into a tuberculin syringe, and the syringe is labelled "R". 10.0 ml of Phosphate Buffered Saline is poured into a beaker, and set beside the column, for elution of the column.

MCP-1 is labelled with iodine-123 as follows:

To a siliconized microfuge tube reaction vial (1.7 ml), add (12.5 μg) MCP-1 in 0.125 ml 0.05M Phosphate Buffer, pH 6.8. Add (50.0 μl) 0.25M Phosphate Buffer, pH 6.8 to the reaction vial and gently swirl. Add (20 μl) 20 nanograms "cold" iodide and gently swirl. Add (10–20 μl), 2.0 mCi, NaI-123 to the reaction vial and gently swirl. Add (45.0 μl) of Chloramine-T to the reaction vial, with a pre-drawn Hamilton syringe, and gently swirl. Incubate for 1.5 minutes at room temperature.

Add (45.0 μl) of Metabisulfite to the reaction vial, with a pre-drawn Hamilton syringe, and gently swirl. Assay reaction vial on a Capintec dose calibrator.

After reaction mixture has been assayed, place entire volume on prepared AG1-X8 column. Add (50 μl) PBS to reaction vial and swirl, then add to reaction mixture on column. Unplug column and collect 8 drops in the first tube. Then collect 2 drops in the next 24 tubes. The Vo will be in approximately tube #6. Use 1.7 ml siliconized microfuge tubes. Assay collected fractions on the Capintec dose calibrator. Combine the major fractions starting at the void volume. (NOTE: An aliquot should be taken for a dose assay for accurate results, if tissue distribution studies are being done.) Run TLC of sample in order to observe any free I-123. Spot a very small aliquot on a Gelman ITLC-SG strip, and develop with N-saline for 8 to 10 minutes. Cut into 1.0 cm sections and count on auto-gamma counter. Unreacted I-123 migrates at or near solvent front, protein remains at origin, small peptides have varying Rf values, at or near the origin.

EXAMPLE 7

Indium-111 Radiolabelling of MCP-1.

The following reagents and materials are prepared prior to running the reaction:

A) Cyclic-Diethylenetriaminepentaacetic acid dianhydride (C-DTPA), FW-357.22 is synthesized and kept in a desiccator, in vacuo, at room temperature.

B) Commercially available Dimethylsulfoxide anhydrous (DMSO) is further purified by fractional freezing at or below 18.4° C. 20 to 25 ml of DMSO is placed in an oven dried 100 ml bottle and tightly capped. The bottle is placed in a slurry ice water bath and swirled until liquid solidifies on the walls of the bottle. An oven dried Pasteur pipet is used to remove remaining liquid. The bottle is capped and stored at room temperature under nitrogen, in a desiccator. Aldrich, 27, 685-5.

C) Nitrogen Gass is grade #5. Airco

D) Phosphate Buffered Saline (PBS)
1. Dissolve Sigma (PBS) prepared powder in 1.0 liter of millipore water.
2. Check pH, should be 7.4 Sigma, 1000-3

E) Phosphate Buffered Saline+5.0% BSA (For equilibration of G-25 column)
1. To 10.0 ml PBS dissolve 0.5 g BSA.
2. Final concentration 50.0 mg/ml BSA.

F) Phosphate Buffered Saline+0.5% BSA (For elution of G-25 column)
1. To 50.0 ml PBS dissolve 0125 g BSA.
2. Final concentration 5.0 mg/ml BSA.

G) G-25, medium grade
1. Weigh out desired amount and swell in PBS for 24 hours.
2. Before use degas for 24 or more hours.
3. 24 hours prior to radiolabelling pour columns and equilibrate and wash with BSA/PBS solutions.
4. Size of columns to be determined experimentally.

H) 0.10M diethylenetriaminepentaccetic acid (DTPA), FW=393.20
1. Weigh out 0.393 gm DTPA and place in 8.0 ml PBS.
2. Adjust pH to 5.4, bring to total volume of 10.0 ml in a volumetric flask. (Needs to become acidic for solubility) Sigma, D-6518

I) Millipore water

J) 111-Indium chloride (111 -InCl3) in 0.05N HCl Nordion International, Kanata, Canada, T209A (NOTE: In order to avoid hydrolysis and trace metal contamination, all reagents should be of the highest purity, DMSO should be purified by fractional freezing, all glassware and instruments should be thoroughly cleaned and rinsed approximately three times with millipore filtered water, and glassware and instruments to be used in the chelation reaction should be oven dried for approximately 24 hours at about 140° C. and cooled in a desiccator.)

The reaction is run as follows:

In step 1, C-DTPA (11.075 mg) is dissolved in 5.0 ml anhydrous DMSO. The tube is covered with parafilm, and gently inverted until the solution becomes clear. To 10 μg lyophilized IL-8 is added 0.5 ml PBS, pH 7.4. Add 0.01 ml (22.32 μg) C-DTPA/DMSO from step #1. Incubate solution, at room temperature, for 50 minutes. Gently swirl solution every 15 minutes. After incubation, place entire volume on the prepared G-25 column. Collect 0.20 ml fractions. Combine fractions at Vo and several fractions after the void volume. For Vo determination, use blue dextran. 111 -InCl3 is assayed on a Capintec dose calibrator and 1.0 to 2.0 mCi of 111-In is pipetted into the MCP-1 tube. The tube is gently swirled and assayed for the amount of radioactivity. The 111-In/MCP-1 solution is incubated for 30 minutes, at room temperature. Excess 111-In is chelated to prevent the formation of indium hydroxide, an insoluble precipitate. The reaction mixture on a G-25 column and eluted with either PBS or 0.50% BSA, PBS. 0.20 ml fractions are collected. Fractions are assayed either on the dose calibrator or dilute aliquots of the fractions for counting on the gamma counter. Combine the fractions at the Vo (protein peak) and fractions after the void volume until the radioactivity levels decline. The excess chelated 111-In is eluted at or near the Vt. The combined Vo fractions are assayed on the dose calibrator and the radiolabelling efficiency are calculated. The empty reaction tube is also assayed to assure transfer of the majority of radioactivity.

EXAMPLE 8

Imaging with radiolabelled MPC-1.

Routinely, images are acquired serially every 15 minutes for 3.0 hours post radiolabel injection. 15 minute images are also acquired every 24 hours post injection, until the labelled MCP-1 is cleared from the animal.

Suitable cameras and collimators are used, with 123-I, 111-In, and Tc-99m. A Siemens, ZLC Orbiter camera and a 140 Kev, high resolution or medium energy collimators are effective. Image acquisition and storage, on all cameras, may be accomplished by a Siemens MicroDelta computer, connected to a larger MicroVAX unit.

MCP-1 material, when carrying a label or radioactive agent in accordance with the present invention, is particularly suitable for imaging sites of inflammation, infectious disease, atheromatous lesion or restenosis. Since many modifications, variations and changes in detail may be made to the described embodiments, it is intended that all matter in the foregoing description be interpreted as illustrative and not in a limiting sense.

---

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 76 amino acids
( B ) TYPE: amino acid
( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:1:

```
Xaa Pro Asp Ala Ile Asn Ala Pro Val Thr Cys Cys Tyr Asn Phe Thr
 1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Lys Thr
65                  70                  75
```

White, male, Sprague-Dawley rats, weighing between 250 and 350 gm are used for imaging of inflammatory lesion. The lesion is induced by injecting 300 μl of 2.0% carrageenan (iota form), suspended in n-saline, into the hind limb. The other hind limb is used as a control and is injected with 300 μl saline. The hind limbs are selected, instead of IP or Sub-Q injections of carrageenan on the body of the rats, because less background activity is present for these studies.

The lesion is induced at various times prior to the injection of the radiolabelled MCP-1. A difference in uptake of radioactivity is observed in the carrageenan limb, as compared to the control limb, when the radiolabelled MCP-1 is injected 3 hours to 24 hours post lesion induction.

We claim:

1. A method of imaging a target site in an animal body, comprising providing a labelled CC chemokine wherein C stands for cysteine, introducing a detectable amount of said labelled CC chemokine into an animal's body, allowing the labelled CC chemokine to accumulate at a target site of the animal's body, wherein Monocyte Chemoattractant Protein (MCP) receptor molecules are located at said target site, and detecting the accumulated, labelled CC chemokine so as to image said target site.

2. The method of claim 1 wherein said target site is a site of infection, inflammation, atheromatous lesion or restenosis of said animal's body.

3. The method of claim 1 wherein said labelled CC chemokine is radiolabelled MCP material.

4. The method of claim 3 wherein said MCP material is labelled with technetium-99m, indium-111, copper-62, or iodine-123.

5. The method of claim 1 wherein said CC chemokine is labelled utilizing a chelating agent.

6. The method of claim 5 wherein said chelating agent is a triamide thiolate ligand, a diamide dithiolate ligand or a diamide diphenolic ligand.

7. The method of claim 6 wherein said CC chemokine is labelled with technetium-99m, rhenium-186, rhenium-188 or copper-62, and said chelating agent is a triamide thiolate ligand.

8. The method of claim 7 wherein said CC chemokine is human MCP-1.

9. The method of claim 6 wherein said CC chemokine is labelled with technetium-99m or copper-62, and said chelating agent is a diamide dithiolate ligand.

10. The method of claim 9 wherein said CC chemokine is human MCP-1.

11. The method of claim 6 wherein said CC chemokine is labelled with technetium-99m, rhenium-186, rhenium-188, copper-62 or indium-111, and said chelating agent is a diamide diphenolic ligand.

12. The method of claim 11 wherein said CC chemokine is human MCP-1.

13. The method of claim 1 wherein said CC chemokine is human MCP-1.

14. A method of delivering a labelling agent to a target site of an animal's body, comprising introducing into an animal's body a CC chemokine carrying a labelling agent, and allowing the labelling agent-carrying CC chemokine to accumulate at a target site which includes Monocyte Chemoattractant Protein (MCP) receptor molecules so as to deliver said labelling agent to said target site.

15. A method of delivering a radioactive agent to a target site of an animal's body comprising introducing into an animal's body a CC chemokine carrying a radioactive agent, and allowing the radioactive agent-carrying CC chemokine to accumulate at a target site which includes Monocyte Chemoattractant Protein (MCP) receptor molecules, so as to deliver said radioactive agent to said target site.

16. The method of claim 15 wherein said target site is a site of atheromatous lesion or restenosis of said animal's body, and wherein the accumulated CC chemokine and radioactive agent therapeutically inhibit proliferation of smooth muscle adjacent said target site.

17. The method of claim 16 wherein said radioactive agent is iodine-131, rhenium-186 or rhenium-188.

18. A composition comprising a CC chemokine carrying a labelling agent selected from the group consisting of technetium-99m, indium-111, copper-62, rhenium-186 and rhenium-188.

19. A composition comprising a CC chemokine conjugated with a chelating agent.

20. The composition of claim 18 wherein said chelating agent is a triamide thiolate ligand, diamide dithiolate ligand or diamide diphenolic ligand.

21. A composition comprising CC chemokine conjugated with a chelating agent carrying a labelling agent.

22. A composition of claim 21 wherein said chelating agent is a triamide thiolate ligand, diamide dithiolate ligand or diamide diphenolic ligand.

23. The composition of claim 21 wherein said labelling agent is a radioactive labelling agent selected from the group consisting of technetium-99m, indium-111, copper-62, rhenium-186 and rhenium-188.

24. The method of claim 1 wherein the labelled CC chemokine is carbon-13 labelled CC chemokine, and said target site is a site of infection, inflammation atheromatous lesion or restenosis, wherein the target site is imaged by magnetic resonance spectroscopy.

25. The method of claim 1 wherein said CC chemokine is a peptide having specificity for a receptor of MCP-1.

* * * * *

UNITED STATES PATENT AND TRADEMARK OFFICE
CERTIFICATE OF CORRECTION

PATENT NO. : 5,413,778
DATED : May 9, 1995
INVENTOR(S) : Steven L. Kunkel et al.

It is certified that error appears in the above-indentified patent and that said Letters Patent is hereby corrected as shown below:

Column 2, line 18, after "COOH," insert —(SEQ ID NO:1)—

Signed and Sealed this

Eighth Day of August, 1995

Attest:

BRUCE LEHMAN

*Attesting Officer*    *Commissioner of Patents and Trademarks*